United States Patent [19]

Los

[11] 4,255,581

[45] Mar. 10, 1981

[54] PROCESS FOR THE PREPARATION OF ALKYL AND ARYL ESTERS OF 3'-SUBSTITUTED AND 2', 3'-DISUBSTITUTED 2-ANILINO-3-PYRIDINECARBOXYLIC ACIDS

[75] Inventor: Mario A. Los, Buenos Aires, Argentina

[73] Assignee: Laboratories Bago, S.A., Capital Federal, Argentina

[21] Appl. No.: 66,081

[22] Filed: Aug. 13, 1979

[51] Int. Cl.$^3$ .............. C07D 213/80; C07D 213/803; C07D 405/02

[52] U.S. Cl. .................................. 546/269; 424/263; 546/310; 546/318

[58] Field of Search ............... 546/269, 298, 318, 310, 546/319, 315

[56] References Cited

U.S. PATENT DOCUMENTS

| | | | |
|---|---|---|---|
| 3,478,040 | 11/1969 | Sherlock | 546/269 |
| 3,697,533 | 10/1972 | Sherlock | 546/298 |
| 3,839,344 | 10/1974 | Sherlock | 546/318 |
| 4,168,313 | 9/1979 | Bago | 546/269 |

FOREIGN PATENT DOCUMENTS

| | | | |
|---|---|---|---|
| 182409 | 1/1971 | Argentina | 546/269 |
| 183423 | 3/1971 | Argentina | 546/269 |
| 2193580 | 2/1974 | France | 546/269 |
| 2187317 | 6/1975 | France | 546/269 |
| (Addition to No. 72-20490) | | | |
| 49-75713 | 7/1974 | Japan | 546/269 |
| 6414717 | 6/1965 | Netherlands | 546/269 |
| 534130 | 4/1968 | Switzerland | 546/269 |
| 534129 | 4/1973 | Switzerland | 546/269 |
| 1147702 | 4/1969 | United Kingdom | 546/269 |
| 1162287 | 8/1969 | United Kingdom | 546/269 |

OTHER PUBLICATIONS

Najer et al., Chem. Abstracts, vol. 78, abst. 111135c (1973) (abst. of Ger. Offen. 2,234,712).

Sherlock, Chem. Abstracts, vol. 79, abst. 18582g (1973) (Abst. of Swiss 534,129).

Najer et al., Chem. Abstracts, vol. 82, abst. 97814x (1975) (abst. of Fr. Demande 2,193,580).

*Primary Examiner*—John D. Randolph
*Attorney, Agent, or Firm*—Kane, Dalsimer, Kane, Sullivan and Kurucz

[57] ABSTRACT

In this disclosure, the synthesis of alkyl and aryl esters of substituted 2-anilino-3-pyridinecarboxylic acids is described. This preparation is performed reacting a previously obtained alkyl or aryl ester of 2-chloro-3-pyridinecarboxylic acid, with 3,2 or 3-substituted aniline.

20 Claims, No Drawings

PROCESS FOR THE PREPARATION OF ALKYL AND ARYL ESTERS OF 3'-SUBSTITUTED AND 2', 3'-DISUBSTITUTED 2-ANILINO-3-PYRIDINECARBOXYLIC ACIDS

BACKGROUND OF THE INVENTION

1. Field of the Invention

The invention relates to a process for the preparation of alkyl and aryl esters of 3'-substituted and 2', 3'-disubstituted 2-anilino-3-pyridine carboxylic acids and more specifically relates to a process for the preparation of pivaloyloxymethyl and 3-phthalidyl esters of 2-[3'-(trifluormethyl) anilino]-3-pyridinecarboxylic and 2-(3'-chloro-2' methylanilino)-3-pyridinecarboxylic acids.

2. Brief Description of the Prior Art

The prior art includes literature teaching the synthesis and use of alkyl and aryl esters of 3'-substituted and 2', 3'-disubstituted 2-anilino-3-pyridine carboxylic acids. For example, the preparation of 2-(3' chloro-2'-methylanilino)-3-pyridinecarboxylic acid, an analgesic agent, was disclosed in British Pat. No. 1.147.702. Also, the synthesis of 2-[3'-trifluoromethyl) anilino]-3-pyridinecarboxylic acid, an antiinflammatory agent, was described in Dutch Pat. No. 6.414.717 and Argentine Pat. No. 183.423.

These 3' and 3', 2'-substituted 2-anilino-3-pyridinecarboxylic acids present in addition to their antiinflammatory and analgesic properties, an ulcerogenic effect on the gastric epithelium. To diminish such side-effects several related derivatives were synthesized. For example, aminoalkyl esters of 2-anilino-nicotinic acids are described in French Pat. No. 2.187.317. Glyceryl esters of the same acids are disclosed in Swiss Pat. No. 534.130 and South African Pat. No. 68 2185. Also, different salts of substituted 2-anilino-3-pyridine-carboxylic acids were described; e.g. ethanolamine, lysine, aluminium and bismuth salts are disclosed in Argentine Pat. No. 182.409, Japanese Pat. No. 74 075713 and British Pat. No. 1.162.287.

The present invention concerns a new process for preparing esters of the above-described acids which lack the characteristic side-effects presented by analgesic and antiinflammatory acids from which these esters are derived (Scherrer, R. A., Whitehouse, M. W., Anti-inflammatory Agents, Chemistry and Pharmacology, 13-1, Academic Press, New York, 1974).

Compounds produced by the method of the invention are antiinflammatory agents which exhibit lessened ulcerogenic effects.

SUMMARY OF THE INVENTION

The invention comprises a process for the preparation of alkyl and aryl esters of 3'-substituted and 2', 3'-disubstituted 2-anilino-3-pyridinecarboxylic acids of the formula:

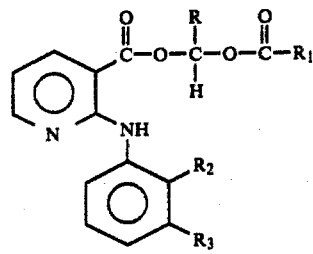

wherein: the

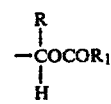

group is selected from the group consisting of an acyloxymethyl group of formula:

$$-CH_2-OCOC(CH_3)_3 \qquad (II)$$

and a heterocyclic structure of formula:

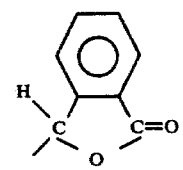

and $R_2$ and $R_3$ are each independently selected from the group consisting of hydrogen, chlorine, methyl and trifluoromethyl, which comprises:

(a) reacting a compound of the formula:

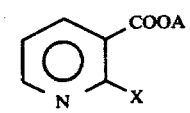

wherein X represents halogen and A is an ammonium radical derived from an amine of the formula:

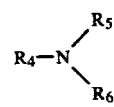

wherein $R_4$, $R_5$ and $R_6$ are each independently selected from the group consisting of hydrogen, acyl, alkyl and the residue of an aliphatic alcohol having 1 to 4 carbon atoms; with a compound of the formula:

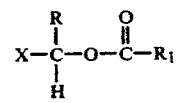

wherein $R_1$ and X are as previously defined;

whereby there is obtained a compound of the formula:

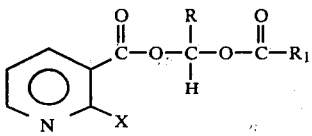

wherein R, R$_1$ and X are as previously defined; and (b) reacting the compound of formula (VII) above with a compound of formula:

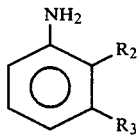

wherein R$_2$ and R$_3$ have the meaning herein before described.

DETAILED DESCRIPTION OF THE PREFERRED EMBODIMENTS OF THE INVENTION

The process of the invention is diagrammatically represented in the following schematic formulae:

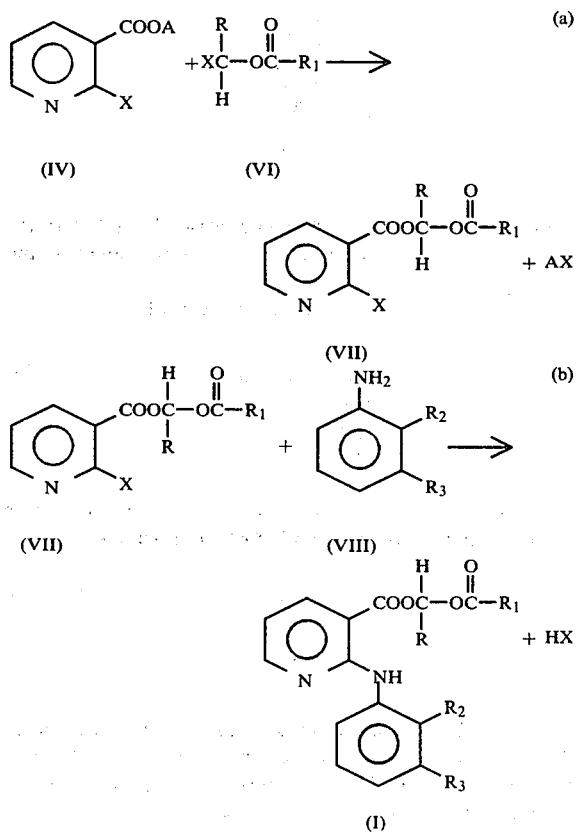

wherein R, R$_1$, R$_2$, R$_3$, A and X have the meanings previously ascribed to them.

As shown in the above reaction scheme, the process of the invention comprises two synthesis steps. In the first step (a) the salified and substituted 2-halogeno-3-pyridine-carboxylic compound (IV) is reacted with a compound of formula (VI) to give alkyl or aryl esters of 2-halo-3-pyridine-carboxylic acid (VII). This reaction is advantageously carried out in a polar reaction medium, wherein the reactants (IV) and (VI) are completely soluble and stable. Representative of such polar reaction mediums are polar solvents such as acetone, acetonitrile, dimethylformamide, dimethylacetamide and the like.

Advantageously the reaction is carried out under substantially anhydrous conditions, using anhydrous reactants (IV) and (VI) and anhydrous solvents to avoid hydrolysis of the reactants of formula (VI). The proportions of reactants (IV) and (VI) is not critical and may be varied in a molar ratio of from 1:1 to 1:5 (compound IV to compound VI). When the compound of formula (VI) is pivaloyloxymethyl chloride, the molar ratio is preferably within the range of 1:1.5 to 1:2.5. The reactants (IV) and (VI) are brought together employing conventional mixing apparatus and techniques.

Advantageously the reaction mixture of the compounds (IV) and (VI) are heated to promote the desired reaction. Temperature ranging from room temperature up to reflux temperature may be employed.

The compounds of the formula (IV) are generally well known and may be prepared by the reaction of 2-halo-3-pyridine-carboxylic acids with lower alkylamines, such as ethylamine triethylamine, cyclohexylamine, trimethylamine, dimethylamine and the like. Preferred as the lower alkylamine is triethylamine. The preparation of the compound of formula (IV) is advantageously carried out in the same polar solvents described above, under substantially anhydrous conditions.

The compounds of formula (VI) are also generally well known as is their preparation. Representative of the compounds (VI) are 3-bromophthalide, pivaloyloxymethyl chloride. [The pivaloyloxymethyl chloride is synthesized by mixing equimolear parts of pivaloylchloride and paraformaldehyde, in the presence of ZnCl$_2$ (method of Rassmussen and Leonard, J. Am. Chem. Soc. 89, 1967], and the like.

Generally, the reaction of the compounds (IV) and (VI) is complete in one to six hours. Upon completion of the reaction, the intermediate compound of formula (VII) may be separated from the reaction mixture by conventional techniques of crystallization, filtration and extraction or the crude reaction mixture may be employed in the second step (b) described above in the schematic formula, without first separating the compounds of formula (VII).

In the second step (b) of the process of the invention, the intermediate alkyl or aryl esters of 2-halo-3-pyridine-carboxylic acid of formula (VII) are reacted with 3 or 2,3-substituted anilines of the formula (VIII) to obtain the desired product compounds of the formula (I). The reaction is advantageously carried out in the presence of an inert solvent. The term "inert solvent" as used herein means a solvent for one or both of the reactants which does not adversely interfere with the desired course of the reaction. Representative of inert solvents are amyl alcohol, toluene, xylene and the like. Alternatively, the reaction may be carried out by simple admixture of the melted reactants.

When carried out in the presence of a solvent, advantageously the second step of the process of the invention is carried out at reflux temperatures, although temperatures down to room temperature may be employed.

During the second step of the process of the invention, for each mol of formed compound (I) a mol of hydrogen halide is formed; in consequence, 2 mols of aniline (VIII), for each mol of ester (VII) are preferably used.

Generally the second step reaction is complete within 2 to 6 hours. Upon completion of the reaction, the desired product compounds of formula (I) may be separated from the reaction mixture by conventional techniques such as solvent extraction, crystallization, filtration and the like.

The separation of the product compounds of formula (I), depends on the properties of each formed compound. Thus, phthalydil esters of 2-halo-3-pyridinecarboxylic acid may be separated by adding water to the reaction medium.

On the other hand, the formed pivaloyloxymethyl ester of 2-halo-3-pyridinecarboxylic acid, may be extracted from its reaction medium, where water was previously added, using chlorinated solvents, preferably methylene chloride.

Formed product compounds of the formula (I) are readily separated from the reaction mixture by cooling the mixture and filtering the crystallized substance. Those compounds (I) may be purified by recrystallization in solvents, such as ethyl acetate, propyl acetate, isobutyl acetate, methanol and n-butanol. If the compounds of formula (I) were obtained by melting the reactants, they can be purified further by crystallization in the same solvents or by treating them with diluted hydrochloric acid.

The following examples describe the manner and process of making and using the invention and set forth the best mode contemplated by the inventor of carrying out the invention, but are not to be construed as limiting.

EXAMPLE 1

Phthalidyl 2-chloro-3-pyridinecarboxylate

To 600 ml of acetone, 31.5 g of 2-chloro-3-pyridinecarboxylic acid is added and suspended by stirring. Triethylamine (40 ml) is added and after 30 minutes 42.6 g of 3-bromophthalide is poured with stirring into the resulting reaction mixture. The mixture is refluxed for 4 hours and then poured into 2000 ml of water at 50° C. To obtain a precipitated compound, the reaction mixture is cooled with continuous stirring. The solid precipitate is collected by filtration, washed with cooled water and then dried under vacuum at a temperature of 40° C. A yield of 38.7 g (67% of theory) of phthalidyl 2-chloro-3-pyridinecarboxylate is obtained (m.p. 137°-8° C.).

I.R. (Nujol) Strong absorption bands at: 1780,1750,1580,1415, 1380,1270, 1245,1225,1140,1060, 995 and 940 cm$^{-1}$.

Elemental Analysis for $C_{14} H_8 N Cl$: Calculated: C 58.05; H 2.78; N 4.84; Cl 12.24; Found: C 58.21; H 3.00; N 4.65; Cl 12.19.

EXAMPLE 2

Pivaloyloxymethyl 2-chloro-3-pyridinecarboxylate

Into a suspension of 2-chloro-3-pyridinecarboxylic acid (23.7 g) in 500 ml of acetone, triethylamine (30.7 ml) is added. After 30 minutes of stirring, pivaloyloxymethyl chloride (22.5 ml) is poured into the reaction mixture, and the resulting mixture heated to reflux for 2 hours. The mixture is then cooled to a temperature of 15°-20° C., and then poured into 1000 ml of cooled water. The resulting mixture is then extracted with methylene chloride (2×100 ml), and the water layer discarded. To the remaining organic extract, 10 g of anhydrous magnesium sulfate is added and then separated by filtration. The organic extract is distilled at normal pressures to separate methylene chloride. When all methylene chloride is distilled off, the distillation is continued under vacuum (0.17 mm Hg) to separate the desired product compound. The distilled product fraction separates at 131°-133° C., and is pivaloyloxymethyl 2-chloro-3-pyridine-carboxylate. Yield: 21.8 g (53.5% of theory).

I.R. (film layer) Strong absorption bands at: 2990, 1745, 1570, 1440, 1290, 1270, 1150, 1130, 1110, 1055, 1030, 1005 and 975 cm$^{-1}$.

Elements Analysis for $C_{12} H_{14} Cl N$; Calculated: C 53.05; H 5.19; Cl 13.05; N 5.15; Found: C 53.09; H 5.29; Cl 13.06; N 4.85.

EXAMPLE 3

Phthalidyl 2-(3'-trifluoromethyl-anilino)-3-pyridinecarboxylate

To 80 ml of xylene, under reflux, m-trifluoromethylaniline (32.2 g) is added. Then, 29 g of phthalidyl 2-chloro-3-pyridinecarboxylate prepared in accordance with Example 1, Supra (divided in two fractions) is poured into the mixture with an interval of 15 minutes between each addition. The reaction mixture so obtained is maintained under reflux for 5 hours, and then cooled by pouring the mixture into an ice/water bath. To allow the complete crystallization of the desired product, the poured reaction mixture is maintained for 2 hours at a temperature of 0°-5° C. The precipitate is collected by filtration and dried under vacuum, at a temperature of 40° C. A yield of 34.1 g (82.3% of theory) of phthalidyl 2-(3-trifluoromethylanilino)-3-pyridinecarboxylate is obtained (m.p. 159°-162° C.). Recrystallizing the compound with 6 volumes of ethyl acetate, 28.4 g (68.5% yield) is obtained (m.p. 164°-5° C.).

I.R. (Nujol) Strong absorption bands at: 3300, 1785, 1695, 1610, 1570, 1520, 1340, 1320, 1260, 1160, 1120, 1090, 1050 and 970 cm$^{-1}$.

Elemental Analysis for $C_{21} H_{13} F_3 N_2 O_4$; Calculated: C 60.87; H 3.16; F 13.76; N 6.76; Found: C 60.50; H 3.22; F 13.62; N 6.79.

EXAMPLE 4

Pivaloyloxymethyl 2-(2'-methyl-3'-chloro-anilino)-3-pyridinecarboxylate

Into a suitable flask, pivaloyloxymethyl 2-chloro-3-pyridinecarboxylate prepared according to Example 2, supra (21.7 g) and 3-chloro-2-methylaniline (28.4 g) are charged. To begin the reaction the mixture is heated to 140° C. During the reaction the temperature of the reaction mixture rises to 190° C. When reaction is completed, the temperature diminishes. The reaction mixture is then cooled to room temperature. Diluted hydrochloric acid is added to the cooled mixture and the precipitated compound ground into small particles and suspended in the reaction mixture. The solid is separated by filtration and the cake washed with water. Then the washed solid is dissolved in hot methanol and recrystallized by cooling the methanolic solution. The crystallized product is separated and dried under vacuum, at a temperature of 40° C. Pivaloyloxymethyl 2-(2'-methyl-3'-chloro-anilino)-3-pyridinecarboxylate (m.p. 90°–91° C.) is so obtained, with a yield of 22.5 g (77.6% of theory).

I.R. (BrK) Strong absorption bands at: 1755, 1710, 1625, 1585, 1530, 1460, 1440, 1405, 1255, 1150, 1110, 1070, 1055 and 975 cm$^{-1}$.

Elemental Analysis for $C_{19}H_{21}ClN_2O_4$; Calculated: C 60.56; H 5.62; Cl 9.41; N 7.43; Found: C 60.67; H 5.59; Cl 9.37; N 7.48.

EXAMPLE 5

Phthalidyl 2-(3'-Chloro-2'-methylanilino)-3-pyridinecarboxylate

Replacing the m-trifluoromethylaniline with 3-chloro-2-methylaniline, Example 3, supra, is repeated. 31.8 g of phthalidyl 2-(3'-chloro-2'-methylanilino)-3-pyridinecarboxylate (m.p. 178°–180° C.) is obtained (Yield: 80.5% of theory).

I.R. (BrK) Strong absorption bands at: 1785, 1710, 1620, 1580, 1425, 1400, 1240, 1050, and 955 cm$^{-1}$.

Elemental Analysis for $C_{21}H_{15}ClN_2O_4$; Calculated: C 63.89; H 3.83; Cl 8.98; N 7.09; Found: C 64.20; H 3.87; Cl 9.21; N 6.89.

EXAMPLE 6

Pivaloyloxymethyl 2-(3'-trifluoromethylanilino)-3-pyridinecarboxylate

Using m-trifluoromethylaniline instead of 3-chloro-2-methylaniline, Example 4, supra, is repeated. 26.5 g of pivaloyloxymethyl 2-(3'-trifluoromethylanilino)-3-pyridinecarboxylate (m.p. 55°–56° C.) is obtained (Yield: 84.3% of theory).

I.R. (BrK) Strong absorption bands at: 1740, 1700, 1615, 1585, 1340, 1260, 1160, 1125, 1085, 1065, 1040, 1010 and 980 cm$^{-1}$.

Elemental Analysis for $C_{19}H_{19}F_3N_2O_4$; Calculated: C 57.57; H 4.83; F 14.38; N 7.07; Found: C 57.72; H 4.60; F 14.40; N 7.30.

What is claimed:

1. A process for the preparation of alkyl and aryl esters of 3-substituted and 2',3'-disubstituted 2-anilino-3-pyridinecarboxylic acids of the formula:

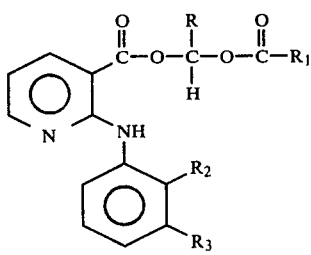

(I)

wherein the

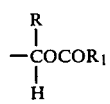

group is selected from the group consisting of an acyloxymethyl group of formula:

—CH$_2$—OCOC(CH$_3$)$_3$ (II)

and a heterocyclic structure of formula:

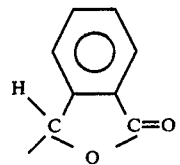

(III)

and R$_2$ and R$_3$ are each independently selected from the group consisting of hydrogen, chlorine, methyl and trifluoromethyl, which comprises;

(a) reacting a compound of the formula:

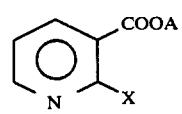

(IV)

wherein X represents halogen and A is an ammonium radical derived from an amine of the formula:

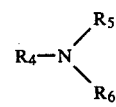

(V)

wherein R$_4$, R$_5$ and R$_6$ are each independently selected from the group consisting of hydrogen, acyl, alkyl and the residue of an aliphatic alcohol having 1 to 4 carbon atoms; with a compound of the formula:

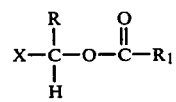

(VI)

wherein R$_1$ and X are as previously defined; whereby there is obtained a compound of the formula:

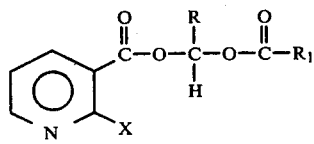

(VII)

wherein R, R$_1$ and X are as previously defined; and (b) reacting the compound of formula (VII) above with a compound of formula:

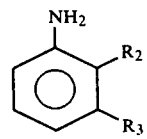

(VIII)

wherein R$_2$ and R$_3$ have the meaning herein before described.

2. The process of claim 1 wherein R$_2$ is methyl and R$_3$ is chlorine.

3. The process of claim 1 wherein R$_2$ is hydrogen and R$_3$ is trifluoromethyl.

4. The process of claim 1 wherein the compound (IV) is prepared by the reaction of 2-chloro-3-pyridinecarboxylic acid with triethylamine, the compound of formula (VI) is 3-bromophthalide and the compound of formula (VIII) is n-trifluoromethylaniline, whereby the product of formula (I) obtained is phthalidyl 2-(3'-trifluoromethylanilino) 3-pyridine carboxylate.

5. The process of claim 1 wherein the compound (IV) is prepared by the reaction of 2-chloro-3-pyridinecarboxylic acid with triethylamine, the compound of formula (VI) is pivaloyloxymethyl chloride and the compound of formula (VIII) is 3-chloro-2-methylaniline, whereby the product obtained is pivaloyloxymethyl 2-(2'-methyl-3'-chloroanilino)-3-pyridinecarboxylate.

6. The process of claim 1 wherein the compound (IV) is prepared by the reaction of 2-chloro-3-pyridinecarboxylic acid with triethylamine, the compound of formula (VI) is 3-bromophthalide and the compound of formula (VIII) is 3-chloro-2-methylaniline, whereby the product of formula (I) obtained is phthalidyl 2-(3'-chloro-2' methylanilino) 3-pyridine carboxylate.

7. The process of claim 1 wherein the compound (IV) is prepared by the reaction of 2-chloro-3-pyridinecarboxylic acid with triethylamine, the compound of formula (VI) is pivaloyloxymethyl chloride and the compound of formula (VIII) is m-trifluoromethylaniline, whereby the product of formula (I) obtained is pivaloyloxymethyl 2-(3'-trifluoromethylanilino)-3-pyridine carboxylate.

8. The process of claim 1 wherein the compound of formula V is triethylamine.

9. The process of claim 1 wherein the reaction of the compound of formula (IV) above with the compound of formula (VI) is carried out in the presence of a polar solvent.

10. The process of claim 9 wherein said solvent is anhydrous acetone.

11. The process of claim 1 wherein the reaction of the compound of formula (VII) with the compound of formula (VIII) is carried out in the presence of an inert solvent at reflux temperatures.

12. The process of claim 11 wherein said solvent is toluene.

13. The process of claim 1 wherein the compounds of formula (VII) and (VIII) are melted and the melted compounds reacted together.

14. The process of claim 1 wherein R is hydrogen and $R_1$ is a tert-butyl group and the product of formula (I) is separated from the reaction mixture by
   (c) adding water to the reaction mixture obtained in step (b);
   (d) extracting the aqueous mixture of (c) with dichloromethane;
   (e) crystallizing the desired product of formula (I) from the extract; and
   (f) filtering the crystals out of the extraction medium.

15. The process of claim 1 wherein the

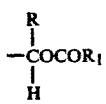

group is a heterocyclic of the formula (III) and desired compound of formula (I) is separated from the reaction mixture of the reaction of compounds (VII) and (VIII) by precipitating it by the addition of water to the reaction mixture.

16. A compound of the formula:

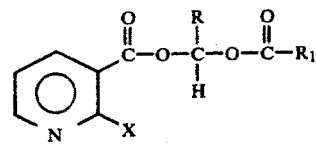 (VII)

wherein the

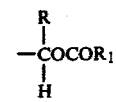

group is selected from the group consisting of an acyloxymethyl group of formula:

 (II)

and a heterocyclic structure of formula:

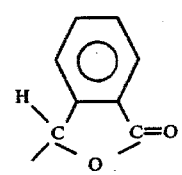 (III)

and X represents halogen.

17. The compound of claim 16 which is phthalidyl 2-chloro-3-pyridine-carboxylate.

18. The compound of claim 16 which is pivaloyloxymethyl 2-chloro-3-pyridine carboxylate.

19. A process for the preparation of alkyl and aryl esters of 3-substituted and 2',3'-disubstituted 2-anilino-3-pyridinecarboxylic acids of the formula:

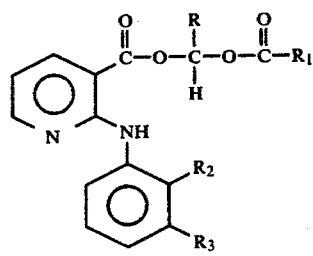 (I)

wherein the

group is selected from the group consisting of an acyloxymethyl group of formula:

 (II)

and a heterocyclic structure of formula:

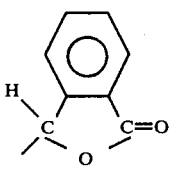
(III)

and $R_2$ and $R_3$ are each independently selected from the group consisting of hydrogen, chlorine, methyl and trifluoromethyl, which comprises;

reacting a compound of the formula:

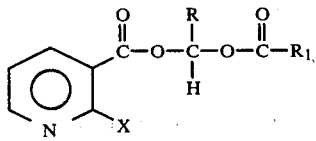
(VII)

wherein R and $R_1$ are as previously defined and X represents halogen; with a compound of the formula:

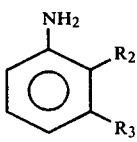
(VIII)

wherein $R_2$ and $R_3$ have the meaning herein before described.

20. A process for the preparation of a compound of the formula:

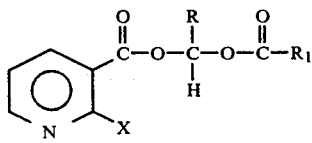
(VII)

wherein X represents halogen and the

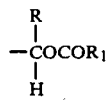

group is selected from the group consisting of an acyloxymethyl group of the formula:

—$CH_2$—$OCOC(CH_3)_3$ (II)

and a heterocyclic structure of formula:

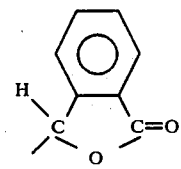
(III)

which comprises;
(a) reacting a compound of the formula:

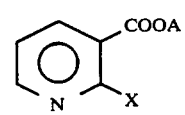
(IV)

wherein X represents halogen and A is an ammonium radical derived from an amine of the formula:

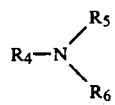
(V)

wherein $R_4$, $R_5$ and $R_6$ are each independently selected from the group consisting of hydrogen, acyl, alkyl and the residue of an aliphatic alcohol having 1 to 4 carbon atoms; with a compound of the formula:

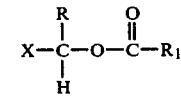
(VI)

wherein $R_1$ and X are as previously defined.

* * * * *